:::

United States Patent
Ryves

(10) Patent No.: US 9,913,914 B2
(45) Date of Patent: Mar. 13, 2018

(54) CELL TRANSPORT

(71) Applicant: Cupid Peptide Company Limited, Cardiff (GB)

(72) Inventor: William Jonathan Ryves, Surrey (GB)

(73) Assignee: CUPID PEPTIDE COMPANY LIMITED, Heath Park, Cardiff (GB)

( * ) Notice: Subject to any disclaimer, the term of this patent is extended or adjusted under 35 U.S.C. 154(b) by 0 days.

(21) Appl. No.: 15/032,668

(22) PCT Filed: Oct. 9, 2014

(86) PCT No.: PCT/GB2014/053037
§ 371 (c)(1),
(2) Date: Apr. 28, 2016

(87) PCT Pub. No.: WO2015/063452
PCT Pub. Date: May 7, 2015

(65) Prior Publication Data
US 2016/0310607 A1 Oct. 27, 2016

(30) Foreign Application Priority Data

Oct. 28, 2013 (GB) .................................. 1318954.3

(51) Int. Cl.
  *A61K 47/48* (2006.01)
  *C07K 7/08* (2006.01)
  *C12N 15/62* (2006.01)
  *C12N 15/87* (2006.01)

(52) U.S. Cl.
  CPC .......... *A61K 47/48246* (2013.01); *C07K 7/08* (2013.01); *C12N 15/62* (2013.01); *C12N 15/87* (2013.01); *C07K 2319/10* (2013.01)

(58) Field of Classification Search
  CPC ................ A61K 47/48246; C07K 7/08; C07K 2319/00; C12N 15/62; C12N 15/87
  See application file for complete search history.

(56) References Cited

FOREIGN PATENT DOCUMENTS

| WO | 00/29427 A2 | 5/2000 | |
| WO | 02/072807 A2 | 2/2002 | |
| WO | 2005/016387 A2 | 2/2005 | |
| WO | WO 2007/109908 A1 * | 10/2007 | ............... C07K 7/06 |
| WO | 2012/023284 A1 | 2/2012 | |
| WO | 2012/170431 A2 | 12/2012 | |

OTHER PUBLICATIONS

Han et al, Efficient Intracellular Delivery of GFP by Homeodomains of *Drosophila* Fushi-tarazu and Engrailed Proteins, Mol. Cells, 2000, 10, pp. 728-732.*
Insulin—*Homo sapiens* from https://www.ncbi.nlm.nih.gov/protein/AAA59172.1, pp. 1-2, accessed Jun. 19, 2017.*
Water, from http://www.biology-online.org/dictionary/Water, pp. 1-3, accessed Apr. 24, 2014.*
GB1318954.3—UK IPO Search Report, dated Jul. 2, 2014.
PCT/GB2014/053037—International Search Report and Written Opinion of the International Searching Authority dated Sep. 17, 2015.
W. Jonathan Ryves, et al., "Use of a Penetratin-Linked Peptide in Dictyostelium", Article in Molecular Biotechnology, vol. 33, 2006, pp. 1-11.
Internet Citation, "Dictyostelium purpureum", pp. 1-2; Jun. 1, 2011. Retrieved on Jan. 19, 2015.
Volker Jager, et al., "High level transient production of recombinant antibodies and antibody fusion proteins in HEK293 cells," BMC Biotechnology 2013, vol. 13, No. 1, Jun. 2013.
F.M. Wurm, "Production of recombinant protein therapeutics in cultivated mammalian cells," Nature Biotechnology, New York, vol. 22, No. 1, Nov. 1, 2004.

* cited by examiner

*Primary Examiner* — Julie Ha
*Assistant Examiner* — Li N Komatsu
(74) *Attorney, Agent, or Firm* — King & Schickli, PLLC

(57) ABSTRACT

The invention relates to novel polypeptides for transporting molecules across cell membranes and, particularly but not exclusively, biological membranes; a conjugate comprising at least one of said polypeptides and at least one selected molecule or agent co-joined or conjugated to said polypeptide for the purpose of transporting said molecule or agent across a cell membrane; a method of transporting at least one selected molecule or agent across a cell membrane involving the use of at least one of said polypeptides; a therapeutic comprising at least one of said conjugates; a combination therapeutic comprising at least one of said conjugates and at least one further therapeutic agent; a method of treatment involving the use of at least one of said conjugates or said therapeutics.

20 Claims, 10 Drawing Sheets

A.

B.

A.

B.

C.

A.

B.

SEQUENCE LISTING

```
<160> NUMBER OF SEQ ID NOS: 13

<210> SEQ ID NO 1
<211> LENGTH: 16
<212> TYPE: PRT
<213> ORGANISM: Dictyostelium discoideum

<400> SEQUENCE: 1

Arg Arg Val Gln Ile Trp Phe Gln Asn Lys Arg Ala Lys Val Lys Arg
1               5                   10                  15

<210> SEQ ID NO 2
<211> LENGTH: 15
<212> TYPE: PRT
<213> ORGANISM: Dictyostelium discoideum

<400> SEQUENCE: 2

Arg Ser Val Gln Ile Trp Phe Gln Asn Arg Arg Ala Lys Ala Arg
1               5                   10                  15

<210> SEQ ID NO 3
<211> LENGTH: 81
<212> TYPE: DNA
<213> ORGANISM: Dictyostelium discoideum

<400> SEQUENCE: 3
gaatccatgc accatcacca tcaccataga agagttcaaa tttggttcca aaataaacgt      60
gctaaagtaa agagaatcga t                                               81

<210> SEQ ID NO 4
<211> LENGTH: 6
<212> TYPE: DNA
<213> ORGANISM: Escherichia coli

<400> SEQUENCE: 4
``` gaatcc 6

<210> SEQ ID NO 5
<211> LENGTH: 18
<212> TYPE: DNA
<213> ORGANISM: Dictyostelium discoideum

<400> SEQUENCE: 5
caccatcacc atcaccat 18

<210> SEQ ID NO 6
<211> LENGTH: 48
<212> TYPE: DNA
<213> ORGANISM: Dictyostelium discoideum

<400> SEQUENCE: 6
agaagagttc aaatttggtt ccaaaataaa cgtgctaaag taaagaga 48

<210> SEQ ID NO 7
<211> LENGTH: 6
<212> TYPE: DNA
<213> ORGANISM: Escherichia coli

<400> SEQUENCE: 7 atcgat 6

<210> SEQ ID NO 8
<211> LENGTH: 16
<212> TYPE: PRT
<213> ORGANISM: Drosophila melanogaster

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 20
<212> TYPE: PRT
<213> ORGANISM: Dictyostelium discoideum

<400> SEQUENCE: 9

Thr Thr Tyr Ala Asp Phe Ile Ala Ser Gly Arg Thr Gly Arg Arg Asn
1               5                   10                  15

Ala Ile His Asp
            20

<210> SEQ ID NO 10
<211> LENGTH: 167
<212> TYPE: PRT
<213> ORGANISM: Homo sapiens

<400> SEQUENCE: 10

Leu Asp Tyr Arg Pro Val Ala Leu Leu Phe His Lys Met Met Phe Glu
1               5                   10                  15

Thr Ile Pro Met Phe Ser Gly Gly Thr Cys Asn Pro Gln Phe Val Val
                20                  25                  30

Cys Gln Leu Lys Val Lys Ile Tyr Ser Ser Asn Ser Gly Pro Thr Arg
            35                  40                  45

Arg Glu Asp Lys Phe Met Tyr Phe Glu Phe Pro Gln Pro Leu Pro Val
        50                  55                  60

Cys Gly Asp Ile Lys Val Glu Phe Phe His Lys Gln Asn Lys Met Leu

```
                65                  70                  75                  80
Lys Lys Asp Lys Met Phe His Phe Trp Val Asn Thr Phe Phe Ile Pro
                    85                  90                  95

Gly Pro Glu Glu Thr Ser Glu Lys Val Glu Asn Gly Ser Leu Cys Asp
                100                 105                 110

Gln Glu Ile Asp Ser Ile Cys Ser Ile Glu Arg Ala Asp Asn Asp Lys
            115                 120                 125

Glu Tyr Leu Val Leu Thr Leu Thr Lys Asn Asp Leu Asp Lys Ala Asn
        130                 135                 140

Lys Asp Lys Ala Asn Arg Tyr Phe Ser Pro Asn Phe Lys Val Lys Leu
145                 150                 155                 160

Tyr Phe Thr Lys Thr Val Glu
                165

<210> SEQ ID NO 11
<211> LENGTH: 44
<212> TYPE: PRT
<213> ORGANISM: Drosophila melanogaster

<400> SEQUENCE: 11

His His His His His His Arg Arg Val Gln Ile Trp Phe Gln Asn Lys
1               5                   10                  15

Arg Ala Lys Val Lys Arg Ile Asp Thr Thr Tyr Ala Asp Phe Ile Ala
                20                  25                  30

Ser Gly Arg Thr Gly Arg Asn Ala Ile His Asp
            35                  40

<210> SEQ ID NO 12
<211> LENGTH: 191
<212> TYPE: PRT
<213> ORGANISM: Homo sapiens

<400> SEQUENCE: 12

His His His His His His Arg Arg Val Gln Ile Trp Phe Gln Asn Lys
1               5                   10                  15

Arg Ala Lys Val Lys Arg Ile Asp Leu Asp Tyr Arg Pro Val Ala Leu
                20                  25                  30

Leu Phe His Lys Met Met Phe Glu Thr Ile Pro Met Phe Ser Gly Gly
            35                  40                  45

Thr Cys Asn Pro Gln Phe Val Val Cys Gln Leu Lys Val Lys Ile Tyr
        50                  55                  60

Ser Ser Asn Ser Gly Pro Thr Arg Arg Glu Asp Lys Phe Met Tyr Phe
65                  70                  75                  80

Glu Phe Pro Gln Pro Leu Pro Val Cys Gly Asp Ile Lys Val Glu Phe
                85                  90                  95

Phe His Lys Gln Asn Lys Met Leu Lys Lys Asp Lys Met Phe His Phe
                100                 105                 110

Trp Val Asn Thr Phe Phe Ile Pro Gly Pro Glu Glu Thr Ser Glu Lys
            115                 120                 125

Val Glu Asn Gly Ser Leu Cys Asp Gln Glu Ile Asp Ser Ile Cys Ser
        130                 135                 140

Ile Glu Arg Ala Asp Asn Asp Lys Glu Tyr Leu Val Leu Thr Leu Thr
145                 150                 155                 160

Lys Asn Asp Leu Asp Lys Ala Asn Lys Asp Lys Ala Asn Arg Tyr Phe
                165                 170                 175

Ser Pro Asn Phe Lys Val Lys Leu Tyr Phe Thr Lys Thr Val Glu
```

-continued

```
                       180                 185                 190

<210> SEQ ID NO 13
<211> LENGTH: 254
<212> TYPE: PRT
<213> ORGANISM: Aequorea victoria

<400> SEQUENCE: 13

Met Arg Arg Val Gln Ile Trp Phe Gln Asn Lys Arg Ala Lys Val Lys
1               5                   10                  15

Arg Ser Lys Gly Glu Glu Leu Phe Thr Gly Val Val Pro Ile Leu Val
            20                  25                  30

Glu Leu Asp Gly Asp Val Asn Gly His Lys Phe Ser Val Ser Gly Glu
        35                  40                  45

Gly Glu Gly Asp Ala Thr Tyr Gly Lys Leu Thr Leu Lys Phe Ile Cys
    50                  55                  60

Thr Thr Gly Lys Leu Pro Val Pro Trp Pro Thr Leu Val Thr Thr Phe
65                  70                  75                  80

Ser Tyr Gly Val Gln Cys Phe Ser Arg Tyr Pro Asp His Met Lys Gln
                85                  90                  95

His Asp Phe Phe Lys Ser Ala Met Pro Glu Gly Tyr Val Gln Glu Arg
            100                 105                 110

Thr Ile Phe Phe Lys Asp Asp Gly Asn Tyr Lys Thr Arg Ala Glu Val
        115                 120                 125

Lys Phe Glu Gly Asp Thr Leu Val Asn Arg Ile Glu Leu Lys Gly Ile
130                 135                 140

Asp Phe Lys Glu Asp Gly Asn Ile Leu Gly His Lys Leu Glu Tyr Asn
145                 150                 155                 160

Tyr Asn Ser His Asn Val Tyr Ile Met Ala Asp Lys Gln Lys Asn Gly
                165                 170                 175

Ile Lys Val Asn Phe Lys Ile Arg His Asn Ile Glu Asp Gly Ser Val
            180                 185                 190

Gln Leu Ala Asp His Tyr Gln Gln Asn Thr Pro Ile Gly Asp Gly Pro
        195                 200                 205

Val Leu Leu Pro Asp Asn His Tyr Leu Ser Thr Gln Ser Ala Leu Ser
    210                 215                 220

Lys Asp Pro Asn Glu Lys Arg Asp His Met Val Leu Leu Glu Phe Val
225                 230                 235                 240

Thr Ala Ala Gly Ile Thr His Gly Met Asp Glu Leu Tyr Lys
                245                 250
```

CELL TRANSPORT

This application is the national stage of international patent application no. PCT/GB2014/053037 filed on Oct. 9, 2014 which in turn claims priority from British Patent Application No. 1318954.3 filed on Oct. 28, 2013, the disclosures of which are incorporated herein by reference in their entirety.

TECHNICAL FIELD

The invention relates to novel polypeptides for transporting molecules across cell membranes and, particularly but not exclusively, biological membranes; a conjugate comprising at least one of said polypeptides and at least one selected molecule or agent co-joined or conjugated to said polypeptide for the purpose of transporting said molecule or agent across a cell membrane; a method of transporting at least one selected molecule or agent across a cell membrane involving the use of at least one of said polypeptides; a therapeutic comprising at least one of said conjugates; a combination therapeutic comprising at least one of said conjugates and at least one further therapeutic agent; a method of treatment involving the use of at least one of said conjugates or said therapeutics.

BACKGROUND

The cell membrane or plasma membrane surrounds the cytoplasm of living cells, physically separating the intracellular components from the extracellular environment. The cell membrane is selectively permeable to ions and organic molecules and controls the movement of substances in and out of the cell. This membrane serves to separate a cell from its surrounding thereby protecting it from changes in the chemical and physical environment, and also permitting regulation of the entry/exit of molecules into and out of the cell. It is made mostly from a bilayer (double layer) of phospholipid molecules, only very few molecules can pass directly through the lipid bilayer to get from one side of the membrane to the other. Embedded within this membrane are a variety of protein molecules that act as channels and pumps for moving vital molecules into and out of the cell. Therefore, it is said that the cell is selective permeable, able to regulate what enters and exits the cell, thus facilitating the transport of materials needed for survival.

Whilst vital biologically, these membranes often pose a difficulty for the delivery of many therapeutics whose efficacy depends upon such molecules being able to travel through the aqueous environment in the body and subsequently across the hydrophobic barrier of cellular membranes.

Cell-permeable or Cell-Penetrating peptides (CPPs) (also known as a protein transduction domain or membrane translocation sequence) are used to overcome the impermeability of the plasma membrane. Typically less than 30 amino acid residues in length, CPPs can traverse the membranes of a cell and access the cell interior, for this reason they have been exploited in a range of living systems to internalize molecules (generically termed 'cargo'). Hundreds of different CPP sequences have now been described and all have a universal capacity to breach biological membranes and enter cells, either alone or when associated with cargo. The function of the CPPs is typically to deliver cargo into cells, a process that commonly occurs through endocytosis with the cargo being delivered via the endosomes of living mammalian cells. Coupling of CPPs to proteins, oligonucleotides, peptide nucleic acids, and other pharmacologically active compounds thus provides a promising strategy for cellular delivery of otherwise membrane-impermeable molecules.

Common applications of CPPs include the delivery of nucleic acid-based macromolecules such as siRNA, antisense oligonucleotide, DNA, and plasmids; all have been realized as promising biological and pharmacological therapeutics in the regulation of gene expression. Recently, it has been reported, using several methods, that CPPs can be used as vehicles to deliver biologically active, full-length proteins, such as horseradish peroxidase, RNase A and even CPP-crosslinked Fab fragments, into living cells.

Broadly speaking, CPPs are generally classified into three groups, but all share the ability to translocate the plasma membrane and facilitate the delivery of various molecular cargoes to the cytoplasm or even to an organelle:

i. short sequences of amino acids with a high density of basic (+) charge, commonly a string of Lysine or Arginine residues e.g. octarginine;

ii. Viral peptides, of which the trans-activating transcriptional activator (TAT) sequence from HIV is the most studied; or iii. The Antennapedia peptide, and derivatives thereof, a key transcription factor discovered within the Antennapedia protein in the 1990s involved in the development of *Drosophila*.

Additionally, or alternatively, CPPs may be classified based upon their peptide sequences and binding properties to lipids: primary amphipathic; secondary amphipathic; and non-amphipathic CPPs.

Mechanistically, the ability of CPPs to translocate a membrane is an on-going area of research. It is thought that the mechanism of action and can vary from one CPP to the next, with some CPPs employing more than one mechanism. Generally, it is thought CPPs enter via: 1) direct penetration of the membrane; 2) endocytosis-mediated entry; or 3) translocation through the formation of a transitory structure.

Direct penetration has recently been proposed to involve strong interactions between cell-penetrating peptides and the phosphate groups on both sides of the lipid bilayer, the insertion of charged side-chains that nucleate the formation of a transient pore, followed by the translocation of cell-penetrating peptides by diffusing on the pore surface.

Endocytosis is the process of cellular ingestion by which the plasma membrane folds inward to bring substances into the cell, but is largely thought to be energy dependent.

In contrast, the third class of CPPs have the property of being internalized by cells through a mechanism that is independent of classic endocytosis. Although the physics of this mechanism is more poorly understood, unlike the other classes, peptides of class 3 can transverse membranes and require no biological surface receptor or cell-derived ATP energy to do so.

In addition to Antennapedia peptide sequence (pAnt), an example of this class 3 includes the synthetically derived PENETRATIN™ CPP, a 16 amino acid peptide derived from the DNA binding domain of the Antennapedia homeoprotein, which is one of the most commonly used CPPs.

Although the class 3 Antennapedia peptide sequence (pAnt) is found within the genome of creatures as diverse as Man, Mouse, Fly and the simple earth worm, there is no Antennapedia sequence in the genome of the eukaryotic *Dictyostelium* amoeba.

We herein disclose the identification of two novel class 3 CPPs from the genome of the social amoeba *Dictyostelium discoideum*, herein termed CUPID A and CUPID B in reference to their origin (Cellular Permeating peptides In *Dictyostelium*). The incorporation of these sequences into larger polypeptides or protein sequences, using recombinant methods, provides products that can permeate cells whilst retaining their polypeptide or protein functionality. Advantageously, these CUPID peptides have been shown to result in superior transport of cargo into cells when compared to other tested CPPs, such as the commonly used PENETRATIN™ CPP, and therefore the CUPID peptides offer improved transport performance for the intracellular delivery of otherwise cell impermeable molecules.

SUMMARY

According to a first aspect of the invention there is provided a cell penetrating peptide (CPP) for transporting a selected molecule or agent across a cellular membrane comprising a peptide having an amino acid sequence selected from the group comprising:
 i) RRVQIWFQNKRAKVKR (SEQ ID NO: 1);
 ii) RSVQIWFQNRRAKAR (SEQ ID NO: 2); or
   a sequence at least 75% homologous to peptide i) or ii).

Reference herein to a CPP refers to a short peptide sequence, typically less than 30 amino acids, that possesses the ability to translocate the plasma membrane when co-joined with at least one selected molecule, whereby the delivery of said molecule inside a cell or an organelle is facilitated.

Reference herein to a cellular membrane or cell membrane includes reference to a biological membrane or an artificial or synthetic membrane based upon, or having, the same or similar properties to a biological membrane (plasma membrane and all intracellular membranes) of Eukaryotic or Prokaryotic origin and so includes reference to artificial or manmade organisms.

In a preferred embodiment of the invention said cellular membrane is a biological membrane.

Reference herein to a biological membrane is to a naturally occurring or living membrane, as opposed to an artificial or synthetic membrane.

As will be appreciated by those skilled in the art, reference herein to selected molecule or agent refers to any cargo that can be co-joined or conjugated to the CPP for the purpose of being transported into a cell or organelle, such as but not limited to, small molecules, proteins and supramolecular particles including peptides, proteins, plasmid DNA, nucleic acid sequences including siRNA and antisense oligonucleotides, chemical entities, therapeutic drugs, antibodies, organic dyes, fluorescent labels, or contrast agents such as quantum dots or nanospheres.

As will be appreciated by those skilled in the art, said biological membrane may be the membrane surrounding a cell. This may include, but is not limited to, membranes such as the simple plasma membrane or more specialized membrane structures including apical, basolateral, presynaptic and postsynaptic membranes, membranes of flagella, cilia, microvillus, filopodia and lamellipodia, the sarcolemma of muscle cells, as well as specialized myelin and dendritic spine membranes of neurons. Additionally, or alternatively, said membrane may be that of an organelle located within the cell, permitting delivery of selected agents to a specific internal cellular compartment. This may include organelles such as, but not limited to, endosome; smooth and rough endoplasmic reticulum; sarcoplasmic reticulum; Golgi apparatus; lysosome; mitochondrion (inner and outer membranes); nucleus (inner and outer membranes); peroxisome; vacuole; cytoplasmic granules; cell vesicles (phagosome, autophagosome, clathrin-coated vesicles, COPI-coated and COPII-coated vesicles) and secretory vesicles.

Additionally, said biological membrane includes reference to any membrane of Eukaryotic or Prokaryotic origin.

The skilled person will appreciate that homologues or derivatives of the CPPs of the invention will also find use in the context of the present invention. Thus, for instance CPPs which include one or more additions, deletions, substitutions or the like are encompassed by the present invention. In addition, it may be possible to replace one amino acid with another of similar "type". For instance, replacing one hydrophobic amino acid with another one can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

The term "homologous" as used herein refers to amino acid sequences which have a sequence at least 75% homology or identity to/with the amino acid sequence of RRVQIWFQNKRAKVKR (SEQ ID NO: 1) or RSVQIWFQNRRAKAR (SEQ ID NO: 2) and which retain the biological activity or membrane transport function of RRVQIWFQNKRAKVKR (SEQ ID NO: 1) or RSVQIWFQNRRAKAR (SEQ ID NO: 2). It is preferred that homologues are at least 75% homologous to the peptide sequence of i) or ii) and, in increasing order of preference, at least 76%, 77%, 78%, 79%, 80%, 81%, 82%, 83%, 84%, 85%, 86%, 87%, 88%, 89%, 90%, 91%, 92%, 93%, 94% 95%, 96%, 97%, 98% or 99% homologous to RRVQIWFQNKRAKVKR (SEQ ID NO: 1) or RSVQIWFQNRRAKAR (SEQ ID NO: 2).

In yet a further preferred embodiment of the first aspect of the invention, said CPP comprises, or consists of, the sequence RRVQIWFQNKRAKVKR (SEQ ID NO: 1) or RSVQIWFQNRRAKAR (SEQ ID NO: 2).

According to a second aspect of the invention, there is provided a conjugate comprising at least one of said CPPs and at least one selected molecule or agent that is covalently or non-covalently attached to or associated with said CPPs for the purpose of transporting said selected molecule or agent across a membrane, typically, but not exclusively, a biological membrane.

In a preferred embodiment of the second aspect of the invention, said selected agent may be attached to said CPP by numerous means as known to those skilled in the art, such as but not limited to, covalent or non-covalent linkage. Alternatively, and more preferably, said cargo will be added to said CPP by in vivo or in vitro recombination.

Ideally, said selected agent will be conjugated to said CPP molecule at either its amino or carboxy terminal.

In a further preferred embodiment of the second aspect of the invention, said selected molecule or agent is conjugated immediately next to or to the amino acid residues of said CPP. Alternatively, said selected molecule or agent is located distally from the amino acid residues of said CPP due to the presence of at least one further amino acid residue or a spacer preferably represented by a number of amino acid residues selected from the group comprising 2, 3, 4, 5, 6, 7, 8, 9, 10, 11, 12, 13, 14, 15, 16, 17, 18, 19, and 20 amino acid residues. As will be appreciated by those skilled in the art, this may improve permeability of the selected agent, however, other spacers that can perform this function to equal effect may be used in the working of the invention.

In a third aspect of the invention there is provided a method of transporting at least one selected molecule or agent across a cellular membrane comprising the use of at least one of said CPPs covalently or non-covalently associated with at least one molecule or agent to be transported across said membrane.

In yet a further aspect of the invention there is provided a therapeutic comprising at least one CPP in accordance with the invention, covalently or non-covalently associated with a selected molecule or agent wherein said molecule or agent is a therapeutic.

As will be appreciated by those skilled in the art, said therapeutic may be a small molecule chemical inhibitor or activator, a protein, a supramolecular particle including a peptide, a plasmid DNA, a nucleic acid sequence including siRNA and an antisense oligonucleotide, a chemical entity, a therapeutic drug, or an antibody. This therefore encompasses the delivery of agents intracellularly to exert their therapeutic action inside the cytoplasm or individual organelles such as, for example, the nuclei for gene therapy to achieve expression of a deficient or incorrectly expressed gene product, delivery of deficient lysosomal enzymes in lysosomes for disease therapy, and proapoptotic anticancer drugs in mitochondria for cancer therapy.

In yet another aspect, there is provided a combination therapeutic comprising at least one CPP covalently or non-covalently associated with a therapeutic agent and one further therapeutic agent. Thus, other active materials may also be present, as may be considered appropriate or advisable for the disease or condition being treated or prevented. For example, the combination therapeutic may also contain an antibiotic or antibacterial agent.

Ideally, said combination therapeutic comprises a plurality of CPPs in accordance with the invention, each one being covalently or non-covalently associated with a therapeutic agent. Ideally the said agents are selected to treat the same condition, ideally different aspects or symptoms thereof, but in certain circumstances they may be selected to treat different conditions from which a patient is suffering. Thus the CPPs of the invention can be used in combination with a selection of therapeutics to enable bespoke treatment to take place.

In yet another aspect, the invention provides a method of treatment comprising administering an effective amount of a therapeutic in accordance with the invention, or combination therapeutic in accordance with the invention, to an individual to be treated.

In yet another aspect of the invention there is provided a pharmaceutical composition comprising a therapeutic in accordance with the invention, or combination therapeutic in accordance with the invention, together with a pharmaceutically acceptable carrier.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intraperitoneal, intravenous and intradermal) administration and may be prepared by any methods well known in the art of pharmacy.

The route of administration will depend upon the condition to be treated but preferred compositions are formulated for intravenous, parenteral, oral, nasal, bronchial or topical administration.

The composition may be prepared by bringing into association the therapeutic of the invention, or combination therapeutic of the invention, and the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a peptide of the invention in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compositions may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Parenteral formulations will generally be sterile.

According to yet a further aspect of the invention there is provided a nucleic acid molecule encoding the CPP according to the invention.

According to yet another aspect of the invention there is provided a nucleic acid molecule encoding the conjugate or therapeutic according to the invention.

According to yet another aspect of the invention there is provided a vector comprising said nucleic acid molecule.

According to yet another aspect of the invention there is provided a host cell transformed or transfected with said vector.

According to yet another aspect of the invention there is provided a method for the production of said CPP, or said conjugate, or said therapeutic, comprising culturing a host cell transformed with a nucleic acid molecule encoding said CPP, or said conjugate, or said therapeutic according to the invention under conditions that enable transcription and translation of said CPP and/or conjugate and/or said therapeutic to take place and then harvesting same.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

BRIEF DESCRIPTION OF THE DRAWINGS

Moreover, unless stated otherwise, any feature disclosed herein may be replaced by an alternative feature serving the same or a similar purpose.

The Invention will now be described by way of example only with reference to the Examples below and to the following Figures wherein.

TABLE 1. AMINO ACID SEQUENCE OF DISCLOSED MOLECULES

Figure 1:
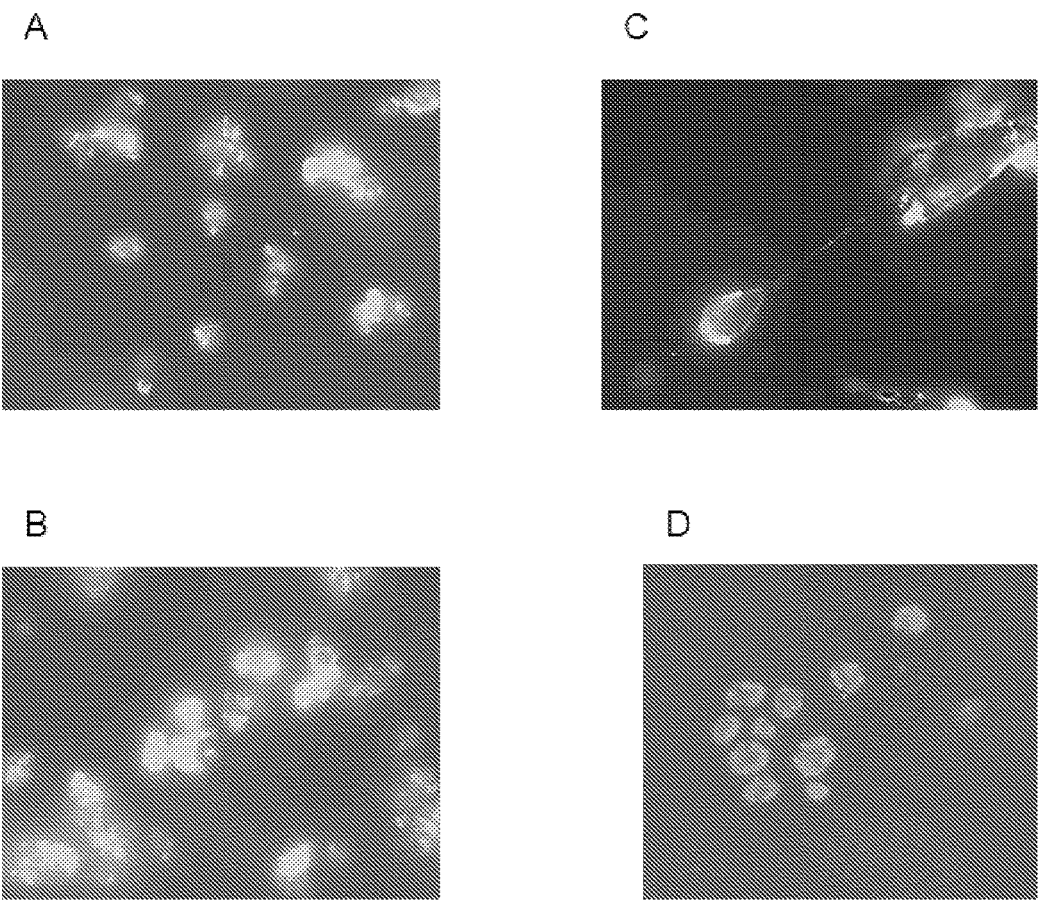
FIG. 1. Fluorescently labeled peptides (10 µM) entering cultured cells after 1 hour. (A) FITC-Cupid A in a *Dictyostelium* cell, (B) FITC-Cupid B in a *Dictyostelium* cell, (C) FITC-Cupid B in Human Fibroblast cell, (D) FITC-Cupid B in human kidney cell.

Materials and Methods
Generation of Cupid-Linked Peptides
Creating the Cupid B Vector
Vector Base pBR322 (New England Biolabs) DNA Vector was cut with EcoRI and ClaI DNA restriction enzymes (New England Biolabs). Samples were incubated in Restriction Enzyme buffer from the manufacturer and incubated at 37° C. with EcoRI (1 µl) and ClaI (1 µl) restriction enzyme leading to a linear DNA molecule (a). This molecule features 'sticky' EcoRI and Cla1 sites at the ends. Samples were stored on ice or frozen at −20° C.

The Cupid B Insert Sequence

The Initial Cupid B Insert sequence, [GAATCCATGCACCATCACCATCACCATAGAAGAGTTCAAATTTGGTTCCAAAATAAAC GTGCTAAAGTAAAGAGAATCGAT] (SEQ ID NO: 3) was ordered synthesized as 2 complimentary DNA strands (Sigma, UK). It features the EcoR1 Restriction Enzyme site (GAATCC; SEQ ID NO: 4), the start codon (ATG), a 6× Histidine (CACCATCACCATCACCAT; SEQ ID NO: 5) the Cupid B sequence (AGAAGAGTTCAAATTTGGTTCCAAAATAAACGTGCTAAAGTAAAGAGA; SEQ ID NO: 6) and the Cla1 Restriction Enzyme site (ATCGAT; SEQ ID NO: 7).

These complimentary strands were annealed together by mixing, heating and cooling and cut with EcoRI and ClaI DNA restriction enzymes (New England Biolabs). Samples were incubated in Restriction Enzyme buffer from the manufacturer and incubated at 37° C. with EcoRI (1 µl) and ClaI (1 µl) restriction enzymes leading to the double-stranded Cupid B insert DNA with ECoR1 and Cla1 'sticky ends' (b). Samples were stored on ice or frozen at −20° C.

The Cupid B Vector

The linear DNA vector (a) was mixed with the Cupid insert (b) and ligated through the 'sticky ends' into a circle with DNA Ligase kit (New England Biolabs). The DNA was cloned into E. Coli bacteria and plated onto LB agar plates supplemented with Ampicillin (100 micrograms per mL). Plasmid DNA was extracted from ampicillin-resistant bacterial colonies and the plasmid sequences were determined (Dundee Sequencing, UK). A clone containing the correct sequence was grown and the Plasmid extracted (Plasmid extraction kit, Qiagen) to provide a source of the finished Cupid B plasmid vector (c). Briefly, clones were grown on LB agar plates supplemented with Ampicillin (100 micrograms per mL). A single colony was picked and grown in LB medium containing Ampicillin for 8 h at 37° C. Cultures were diluted 1/500 in LB supplemented with Ampicillin and grown overnight at 37° C. Cultures were pelleted by centrifugation, followed by lysis and purification according to manufacturers' instructions (Plasmid extraction kit, Qiagen)

Creating the Cupid B-Cargo DNA Plasmid
Cargo DNA Insert

Cargo DNA insert was created from Genomic DNA using PCR amplification technique. The primers for this reaction were synthesized and ordered from Sigma, UK.

Forward Primer: [ClaI site]-Cargo Start DNA
Reverse Primer: Cargo End DNA—Stop Codon—[HindIII site]

The amplified DNA from the PCR reaction was purified (PCR Purification kit, Qiagen) treated with Cla1 and HindIII restriction enzymes and gel purified (Gel purification Kit, Qiagen). This final Cargo DNA insert (e) molecule features 'sticky' Cla1 and HindIII sites at the ends.

Cupid B vector (c) was cut with ClaI and HindIII DNA restriction enzymes (New England Biolabs). Samples were incubated in Restriction Enzyme buffer from the manufacturer and incubated at 37° C. with HindIII (1 µl) and ClaI (1 µl) restriction enzyme leading to a linear DNA molecule (d). This molecule features 'sticky' Cla1 and HindIII sites at the ends. Samples were stored on ice or frozen at −20° C.

The linear Cupid B vector DNA (d) was mixed with the Cargo insert DNA (e) and ligated through the 'sticky ends' into a circle with DNA Ligase kit (New England Biolabs). The DNA was cloned into E. Coli bacteria and plated onto LB agar plates supplemented with Ampicillin (100 micrograms per mL). Plasmid DNA was extracted from ampicillin-resistant bacterial colonies and the plasmid sequences were determined (Dundee Sequencing, UK). A clone containing the correct sequence was grown and the Plasmid extracted (Plasmid extraction kit, Qiagen) as detailed above to provide the finished Cupid B-Cargo DNA plasmid (f)

E. coli strain BL21(DE3) was transformed with 10 ng of the appropriate plasmid, transferred to 1 L LB broth supplemented with Ampicillin (100 µg/mL) and grown overnight at 37° C. to mid-log phase (A600=0.5-0.6). Peptides were induced with 1 mM IPTG for 3 h and the bacteria were harvested by centrifugation. Bacterial pellets were lysed by sonication in 4 volumes of buffer A (50 mM phosphate buffer, 15 pH 7.5, 400 mM NaCl, 2 mM EDTA, 1 mM PMSF). After centrifugation (16,000 g, 15 min) the supernatant was passed through a Ni-NTA His Binding Resin. Where necessary, a Poly Histidine amino tail was added to constructs, using conventional techniques, to allow the product to stick to the Ni-NTA His Binding Resin and be separated from contaminants. Bound peptide was washed with buffer A and eluted by applying an Imidazole gradient (0 to 0.5M in buffer A). The eluted peptide (3 mg/L of culture) was dialyzed against 50 mM phosphate buffer, pH 7.5, 150 mM NaCl overnight. For long term storage, peptides were finally dried and stored at −20 C until use.

Fluorescent Labeling of Peptides and Microscopy

Peptides were labelled with Fluorescein isothiocyanate (FITC) using a FITC labeling kit as per instructions (Pierce, UK). When added to cell cultures the labeled peptides were visualized using a fluorescent microscope by exciting the FITC with a 488 nm spectral line, argon-ion laser (Excitation wavelength of 494 nm and an Emission wavelength of 518 nm).

Dictyostelium Cell Culture

AX2 wild type Dictyostelium cells were grown on SM agar plates seeded with Aerobacter aerogenes bacteria (also known as Klebsiella aerogenes) as a food source.

Results
Establishing Cupid A and Cupid B are CPPs

Figure 2:
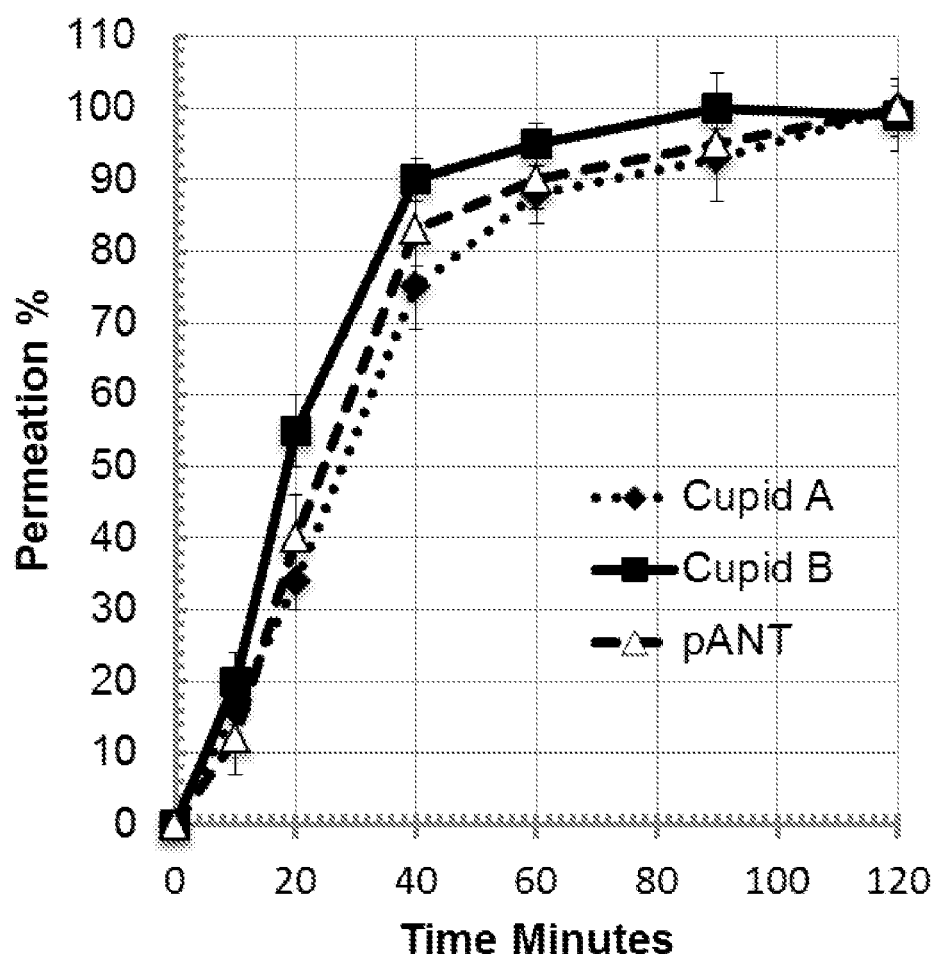
FIG. 2. Time course of fluorescently labelled peptide (10 micromolar of Cupid A, Cupid B or pANT) accumulation within cultured *Dictyostelium* cells.

Cupid A (RSVQIWFQNRRAKAR; SEQ ID NO: 2) and Cupid B (RRVQIWFQNKRAKVKR; SEQ ID NO: 1) were chemically synthesized labelled with FITC at the amino terminal. The peptides were added to cultured eukaryotic cells of Dictyostelium discoideum amoeba for varying amounts of time up to 2 hours. Cells were then washed and prepared for examination under a fluorescent microscope (FIG. 1). The time courses of permeation were compared to the class 3 CPP, the Antennapedia peptide, pANT which was also labelled with FITC in chemical synthesis (FIG. 2).

In other experiments we also found that the permeation capabilities of Cupid peptides extended into all cells tested, including human fibroblasts, human embryonic kidney cells (FIG. 1) and chicken neurons (not shown).

Figure 3:
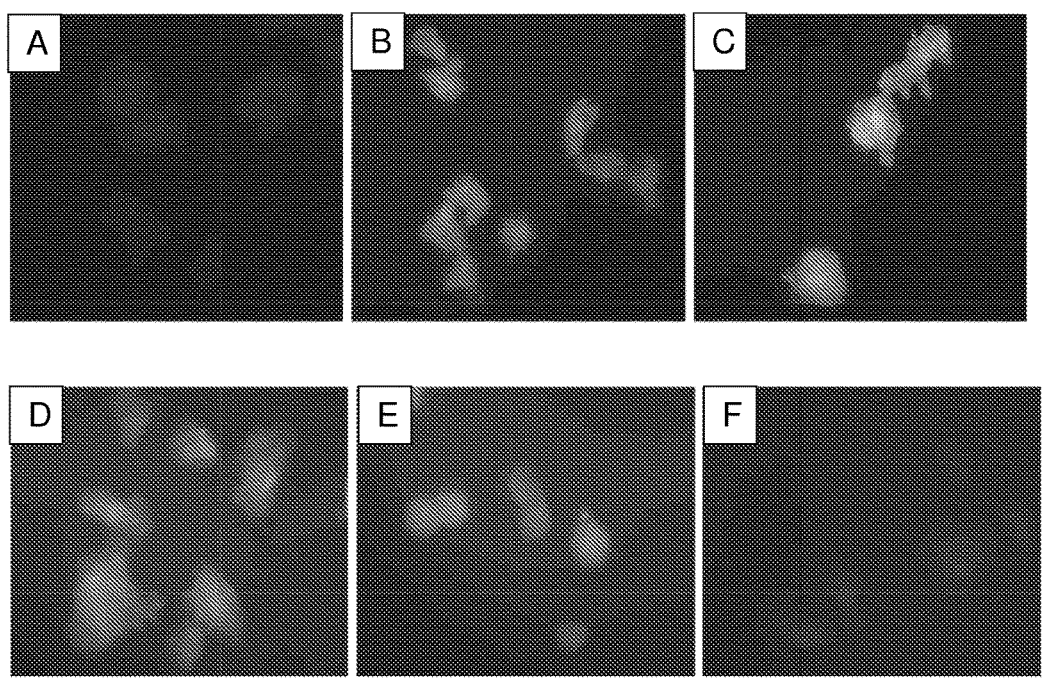
FIG. 3. The accumulation of fluorescently labelled Cupid B peptide (10 micromolar) was monitored in cultured *Dictyostelium* cells (A-C) after 4 min (A), 16 min (B) and 32 min (C). At 32 minutes the culture media was washed out and cell fluorescence monitored (D-E) at 4 min (D), 16 min (E) and 32 min (F) post washing.

We observed that both FITC-labelled Cupid A and Cupid B peptides at 20 micromolar were able to swiftly permeate cells becoming visible within 30 minutes. The uptake reached a maximum within 100 minutes for both peptides, with times for half-maximal permeation being 17 minutes for FITC-Cupid B and 28 minutes for FITC-Cupid A. Under the same conditions FITC-pANT reached half-maximal permeation in 23 minutes. The permeation of FITC-Cupid B was reversible if the media containing the FITC-peptide was replaced with peptide-free media the peptide permeated out of the cells within a similar time period (FIG. 3).

The classification of Cupid A and B as being novel members of the third class of CPP is evidenced by: (i) Ability to enter a variety of living cells; (ii) Capability to exit living cells as well as enter; and (iii) similarity of size and primary structure to the Antennapedia peptide.

Establishing that Cupid can Deliver Bioactive Peptide Cargo Into Living Cells

To examine the ability of Cupid B to be internalized and deliver a bioactive cargo to living cells we have used the *Dictyostelium discoideum* model system.

Upon starvation *Dictyostelium* initiates a developmental program leading to the aggregation of free-living amoebae. Genetic research has uncovered the crucial role that cyclic adenosine monophosphate (cAMP) plays in orchestrating as an extracellular chemoattractant in the initial aggregation process through *Dictyostelium* cAMP-dependent Protein Kinase (DdPKA). DdPKA can be inhibited by PKI, a 20 amino acid peptide sequence derived from an inhibitor of PKA, by PKI binding directly to the catalytic unit of PKA.

By creating a Cupid B-PKI fusion protein we aimed to establish that it prevents starving *Dictyostelium* cells from aggregating in vivo.

Experiments with Cupid B-PKI Peptide Added to Living Cells

Figure 4:
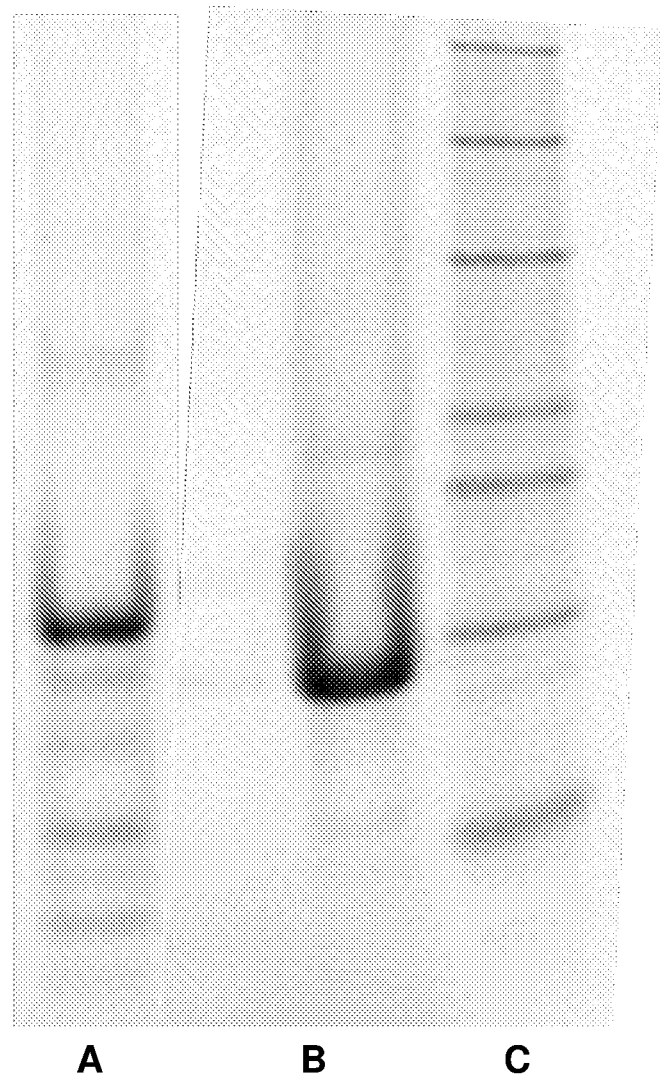
FIG. 4. SDS PAGE gel of dried peptides prepared. The gel was stained with Coomasie Blue protein stain to visualise bands of Cupid-PKI (A), Cupid B (B) and Molecular Weight Standards (C).

Cupid linked peptides were generated as described, and analysed by gel electrophoresis in the presence of SDS this demonstrated the presence of a major band of molecular weight corresponding to that of the Cupid B or Cupid B-PKI peptide (FIG. 4).

Figure 5:
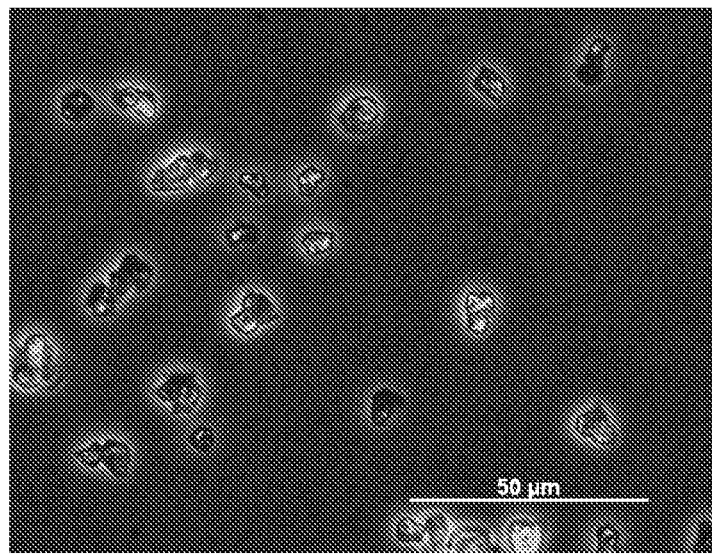
FIG. 5. Fluorescently labeled Cupid B-PKI peptide, 10 micromolar, was added to cultured *Dictyostelium* cells for 1 hour. Cells were then washed and analysed by light (A) and fluorescence (B) microscopy.
Figure 5:
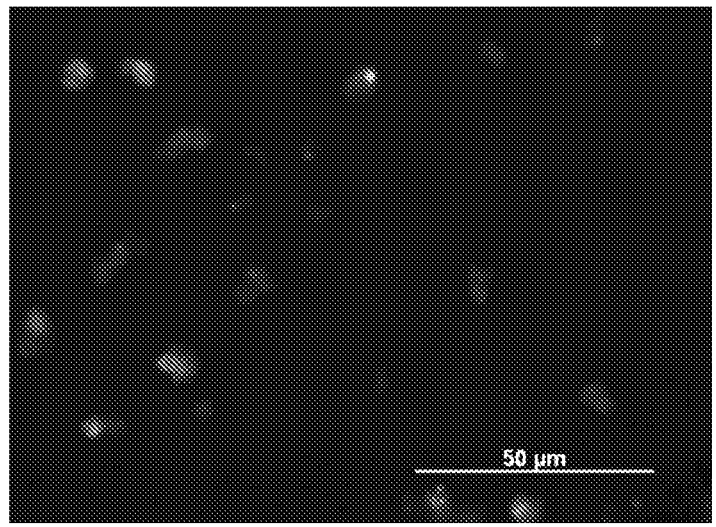

To show that the Cupid B-PKI fusion peptide is capable of permeating into living cells, we labelled the peptide fluorescently using a fluorescein peptide labeling kit (Pierce, UK). Addition of 10 micromolar FITC-Cupid B-PKI to *Dictyostelium* cells for 1 hour followed by fluorescent microscopy showed that Cupid B-PKI is cell permeable (FIG. 5).

Figure 6:
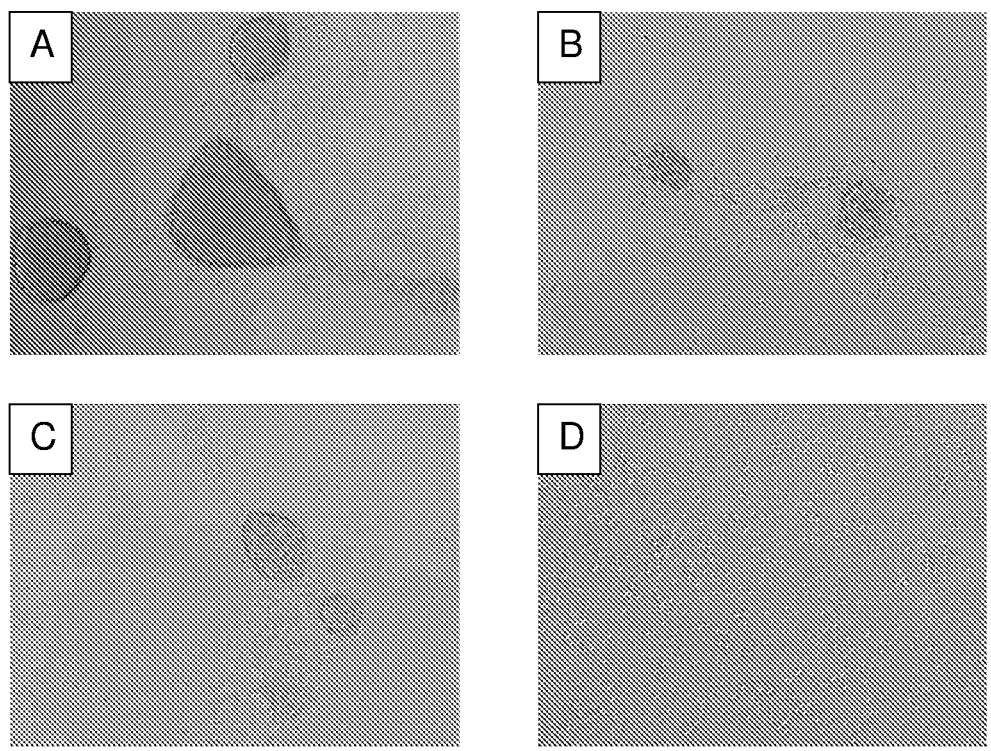
FIG. 6. Cupid can transport small molecule cargo into cells. Starved *Dictyostelium* cultures were treated with no peptide (A), cupid B peptide (B), PKI peptide (C) and Cupid B-PKI peptide (D) and analysed for aggregation. In untreated cultures (A) or cultures treated with 10 micromolar Cupid B peptide (B) or PKI peptide (C), cells aggregated into tight masses. In contrast, cultures treated with 10 micromolar Cupid-PKI peptide (D) failed to aggregate.

We report that the Cupid B-PKI is effective at entering cells and completely attenuating the PKA-dependent process of *Dictyostelium* aggregation at a concentration of 10 micromolar (FIG. 6D). At a similar dose neither the Cupid B peptide nor the PKI peptide alone have any effect on aggregation (FIGS. 6b and c).

Cupid can Deliver Large Peptide Cargo into Cells

Figure 7:
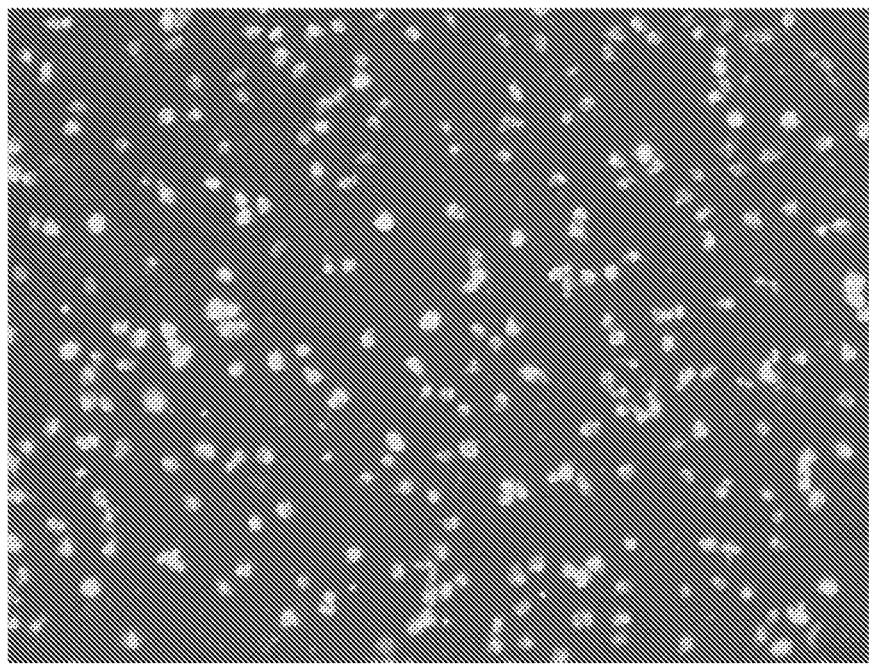
FIG. 7. Fluorescently labeled Cupid B-PTEN peptide, 10 micromolar, was added to cultured *Dictyostelium* cells for 1 hour. Cells were then washed and prepared for fluorescence microscopy.

Using Cupid B to deliver large peptide cargos into living cells, we demonstrated that the Cargo retains bioactivity of both a biological and biochemical nature. To accomplish this we chose a 167 amino acid region of the PTEN protein to fuse to the Cupid B peptide using the process above. This stretch of amino acids (number 186-352 of human PTEN) is known as the C2 region and to be involved in the auto-inhibition of the PTEN enzymatic activity. To show that this large fusion peptide is capable of permeating into living cells, we labelled the peptide fluorescently using a fluorescein peptide labelling kit (Pierce, UK). Addition of 20 micromolar FITC-Cupid B-PTEN to *Dictyostelium* cells for 1 hour followed by fluorescent microscopy showed that Cupid B-PTEN is cell permeable (FIG. 7).

Figure 8:
FIG. 8. Cupid can transport large molecule cargo into the cell. Starved *Dictyostelium* cultures were plated into petri dishes in starvation buffer and visualised after 10 hours. In untreated wild-type (WT) cultures (A), cells stream together into aggregation centres, co-ordinated by cell to cell signaling. In the PTEN null mutant culture (B), or WT cultures treated with 10 micromolar Cupid-PTEN peptide (C), cells failed to stream together or aggregate.
Figure 8:
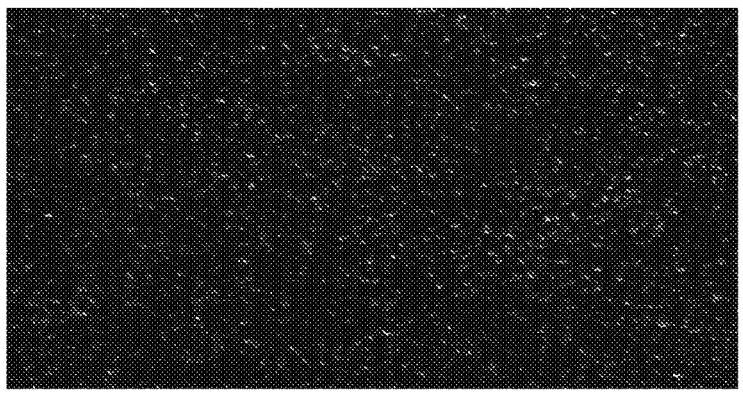
Figure 8:
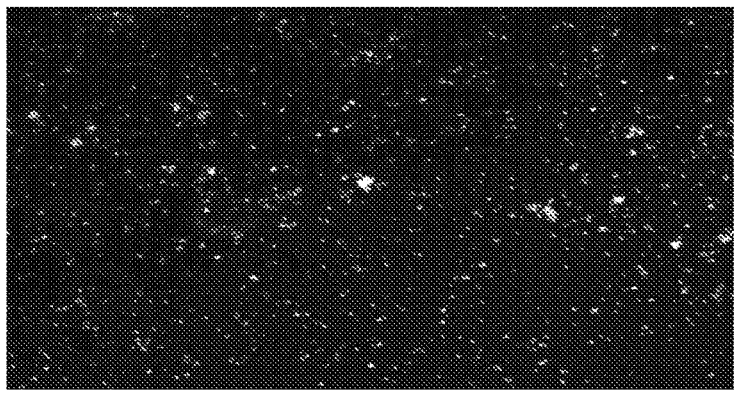

In *Dictyostelium*, a genetic mutant in which the PTEN gene is absent causes marked changes in phenotype. During starvation, for example, the PTEN-null mutant strain exhibits a characteristic aggregation behaviour in which the cells try to aggregate but repeatedly fail to do so when viewed under time-lapse photography (FIG. 8b). If wild-type *Dictyostelium* cells are given the Cupid B-PTEN peptide under these same circumstances at a 10 micromolar dose, they exhibit the same distinctive behaviour as the PTEN-Null strain (FIG. 8c).

The PTEN protein has a phospholipase enzymatic activity that functions to remove phosphate groups from inositol-based lipids and as such is involved with maintaining the balance between varieties of inositol phospholipids present at the cell surface. In wild-type cells undergoing starvation the inositol phospholipids with 3 and 4 phosphate groups (PIP2 and PIP3) are kept low, largely due to the action of PTEN.

Figure 9:
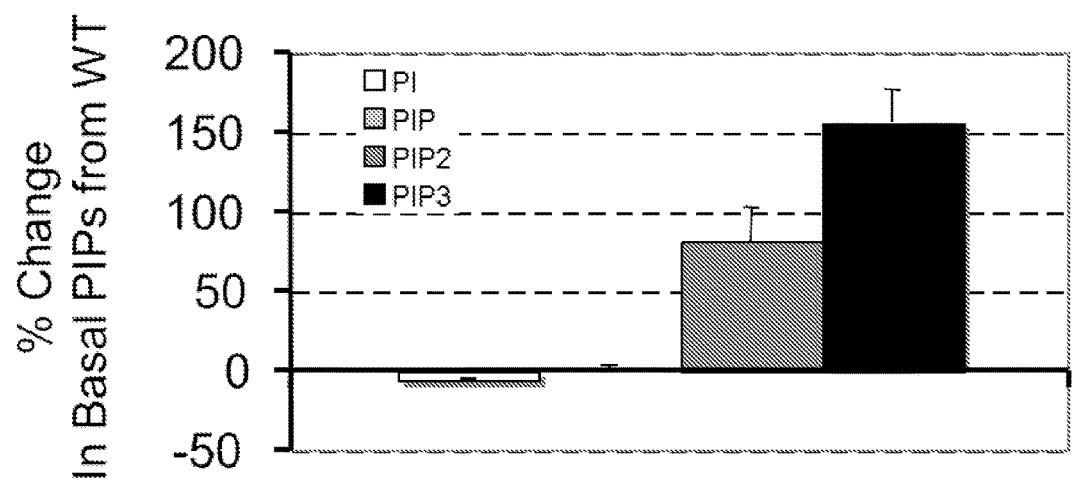
FIG. 9. The levels of the 4 inositol phospholipids (PI, PIP, PIP2 and PIP3) in wild-type *Dictyostelium* cells undergoing starvation were measured by solvent extraction of cell cultures and analysis using thin layer chromatography. The effect of Cupid B-PTEN peptide treatment (10 micromolar, 1 hour) was calculated as a percentage change in the basal (untreated) levels.

We determined the effect of Cupid B-PTEN peptide on the inositol phospholipid levels in *Dictyostelium* cultures. Cupid B-PTEN peptide treated cells (10 micromolar, 1 hour) alters the basal levels of inositol phospholipids in *Dictyostelium* cells. The levels of PIP2 and PIP3 rise to +75% and +150% respectively of untreated basal levels, consistent with inhibition of PTEN phopholipase activity (FIG. 9).

Figure 10:
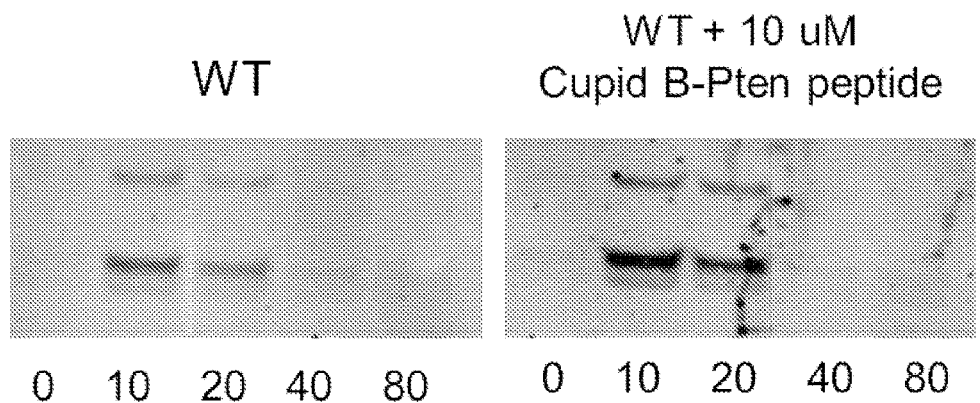
FIG. 10. In starving *Dictyostelium* cultures, several proteins undergo rapid phosphorylation/dephosphorylation events in response to an applied dose of cyclic AMP. The strength of this response is limited by PTEN enzyme activity. This response is visualised with antibody detection of these phosphoproteins on SDS gels prepared from extracted cultures at the time points indicated after the cAMP dose. Compared with wild-type (WT) cultures, cultures pretreated for 1 hour with 10 micromolar Cupid-PTEN peptide, cells exhibited a much greater phosphorylation response suggesting a decreased PTEN activity.

In starving *Dictyostelium* cultures, several proteins undergo rapid phosphorylation/dephosphorylation events in response to an applied dose of cyclic AMP. The strength of this initial phosphorylation response is limited by PTEN enzyme activity and is associated with changes in PIP2 and PIP3 inositol phospholipid levels. When phosphorylation patterns in cultures pretreated for 1 hour with 10 micromolar Cupid B-PTEN peptide were compared with untreated cultures, they exhibited a much stronger initial phosphorylation response to cyclic AMP, providing evidence for a decrease in PTEN activity (FIG. 10).

These data in combination are consistent with the notion that Cupid B-PTEN peptide permeates and inhibits PTEN activity when added to cultures of living cells. This shows that cell-permeant bioactivity of large Cupid B-linked peptides generated by our process is not limited to small cargoes.

Cupid Peptide Can Deliver Large Cargo and Does Not Hinder Cargo Function

To demonstrate that Cupid is effective at performing as a cell permeable peptide carrier we synthesized the Cupid peptide sequence linked to the wild type Green Fluorescent Protein (GFP) from *Aequorea victoria* (Jellyfish; UniProt Accession Number P42212). GFP is a 238 amino acid protein that exhibits bright green fluorescence when exposed to light in the blue to ultraviolet range.

Figure 11:
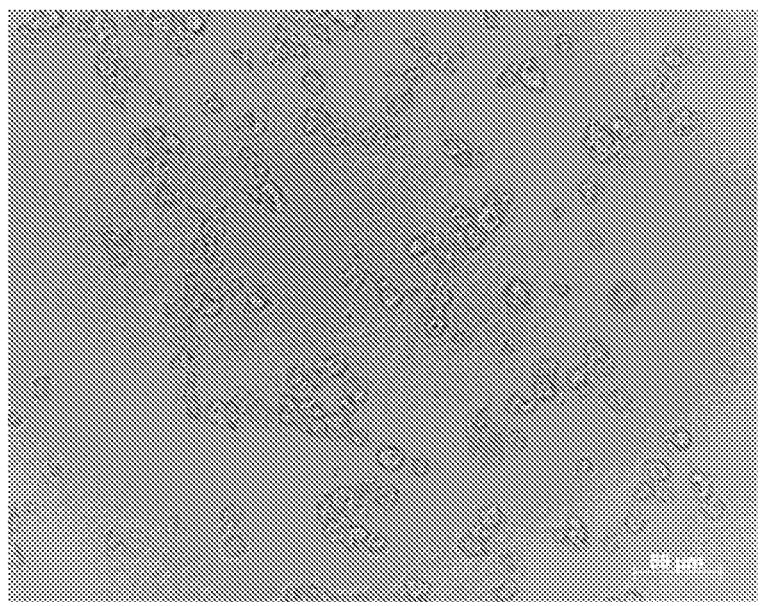
FIG. 11. Cupid can deliver large cargo into cells that is capable of bioactivity. Purified Cupid-GFP (sequence as shown in Table 1), which is not fluorescent, was added to the cell medium at a final concentration of 40 micromolar and incubated for 1 hour. The cells were then washed and mounted on a slide using FLUORSAVE mounting medium (Merck) and observed by microscopy. The cells were observed under phase contrast (A) and fluorescence microscopy (B). GFP was observed leading to the conclusion that Cupid-Green Fluorescent Protein peptide (Cupid-GFP) permeates into cells, refolds and causes these cells to fluoresce.
Figure 11:
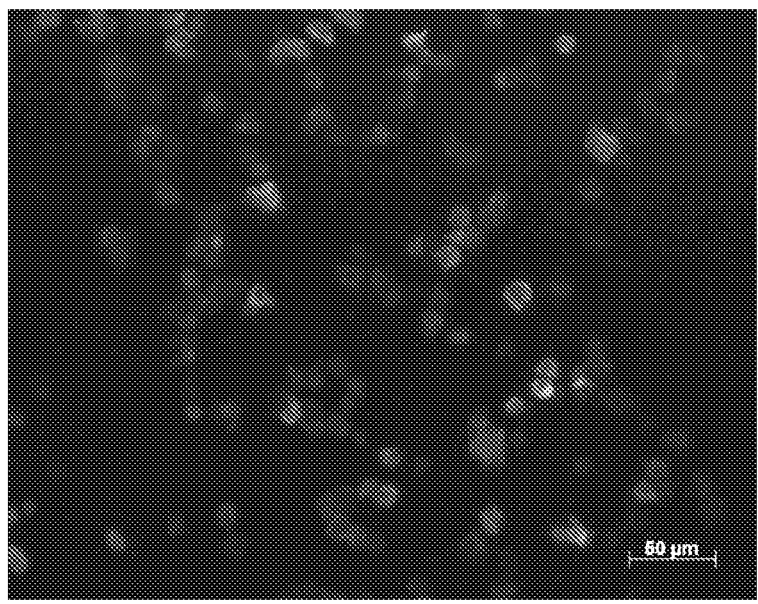

GFP was added to a cupid peptide as shown in Table 1. When Cupid-GFP was purified to a powder and dissolved in distilled water neither the Cupid-GFP powder or the Cupid-GFP solution (1 millimolar) were fluorescent. However, when Cupid-GFP was added to the cell medium (40 µM for 1 h), the cupid-GFP was found to permeate into the cell and begin to fluoresce when observed under fluorescence microscopy (FIG. 11).

The only previous work with a CPP linked to GFP was with TAT and Argx8 CPPS (Lundber, Wikström S, Johansson M. Mol Ther. 2003 July; 8(1):143-50. PMID: 12842437). These GFP peptides were already fluorescent. The authors concluded that the main property of both CPP peptides (and fusion proteins) is to mediate cell surface adherence and that the internalization of these CPPs occurred by endocytosis. However, since here the purified Cupid-GFP is not fluorescent (as it is incorrectly folded) for it to be detectable as green fluorescence suggests that the Cupid-GFP has permeated the cells where it has been correctly folded by the cellular protein machinery. This supports the role of Cupid as a truly cell permeable peptide and can take large cargo peptides into living cells where they are capable of bioactivity.

SUMMARY

We herein disclose the identification of novel peptide sequences (generically termed Cupid) that are capable of traversing cellular membranes, such as biological membranes, thereby acting as a cell penetrating peptides (CPPs). Consequently, these new CPPs can be used to transport and deliver molecules or agents across biological barriers, with potential use for intracellular delivery of a wide range of therapeutic or bioactive molecules.

TABLE 1

| Amino Acid | Sequence |
| --- | --- |
| Cupid A | RSVQIWFQNRRAKAR (SEQ ID NO: 2) |
| Cupid B | RRVQIWFQNKRAKVKR (SEQ ID NO: 1) |
| Antennapedia | RQIKIWFQNRRMKWKK (SEQ ID NO: 8) |

TABLE 1-continued

| Amino Acid | Sequence |
| --- | --- |
| PKI | TTYADRASGRTGRRNAND (SEQ ID NO: 9) |
| PTEN | LDYRPVALLFHKMMFETIPMFSGGTCNPQFVVCQ LKVKIYSSNSGPTRREDKFMYFEFPQPLPVCGDI KVEFFHKQNKMLKKDKMFHFWVNTFFIPGPEETS EKVENGSLCDQEIDSICSIERADNDKEYLVLTLT KNDLDKANKDKANRYFSPNFKVKLYFTKTVE (SEQ ID NO: 10) |
| Cupid B-PKI | HHHHHHRRVQIWFQNKRAKVKRIDTTYADRASGR TGRRNAIHD (SEQ ID NO: 11) |
| Cupid B-PTEN | HHHHHHRRVQIWFQNKRAKVKRIDLDYRPVALLF HKMMFETIPMFSGGTCNPQFVVCQLKVKIYSSNS GPTRREDKFMYFEFPQPLPVCGDIKVEFFHKQNK MLKKDKMFHFWVNTFFIPGPEETSEKVENGSLCD QEIDSICSIERADNDKEYLVLTLTKNDLDKANKD KANRYFSPNFKVKLYFTKTVE (SEQ ID NO: 12) |
| Cupid-GFP | MRRVQIWFQNKRAKVKRSKGEELFTGVVPILVEL DGDVNGHKFSVSGEGEGDATYGKLTLKFICTTGK LPVPWPTLVTTFSYGVQCFSRYPDHMKQHDFFKS AMPEGYVQERTIFFKDDGNYKTRAEVKFEGDTLV NRIELKGIDFKEDGNILGHKLEYNYNSHNVYIMA DKQKNGIKVNFKIRHNIEDGSVQLADHYQQNTPI GDGPVLLPDNHYLSTQSALSKDPNEKRDHMVLLE FVTAAGITHGMDELYK (SEQ ID NO: 13) |

The invention claimed is:

1. A cell penetrating peptide (CPP) for transporting a selected molecule or agent across a cellular membrane, wherein the CPP consists of:
   i) RRVQIWFQNKRAKVKR (SEQ ID NO: 1); or
   ii) a sequence at least 85% homologous to SEQ ID NO: 1.

2. The CPP according to claim 1, wherein said amino acid sequence of part ii) is at least 86%, 87%, 88%, 89%, 90%, 91%, 92%, 93%, 94% 95%, 96%, 97%, 98% or 99% homologous to SEQ ID NO: 1.

3. The CPP according to claim 1, wherein said membrane is naturally occurring or synthetic.

4. The CPP according to claim 1, wherein said membrane is a biological membrane.

5. The CPP according to claim 1, wherein said CPP is co-joined or conjugated to at least one selected molecule or agent for the purpose of transporting said selected molecule or agent across said membrane.

6. The CPP according to claim 5, wherein said CPP is covalently or non-covalently attached to or associated with said selected molecule or agent.

7. The CPP according to claim 5, wherein said selected agent is selected from the group consisting of: small molecules, supramolecular particles, peptides, proteins, plasmid deoxyribonucleic acid (DNA), nucleic acids, small interfering ribonucleic acid (siRNA), antisense oligonucleotides, chemical entities, therapeutic drugs, antibodies, organic dyes, fluorescent labels, quantum dots, and nanospheres.

8. The CPP according to claim 5, wherein said CPP is attached to said selected molecule or agent by in vivo or in vitro recombination.

9. The CPP according to claim 8, wherein said CPP is attached to said selected molecule or agent by in vitro recombination.

10. The CPP according to claim 5, wherein said CPP is conjugated to said selected molecule or agent at either its amino or carboxy terminal.

11. The CPP according to claim 5, wherein said CPP is located distally from said selected molecule or agent due to the presence of at least one further spacer amino acid residue.

12. The CPP according to claim 11, wherein said CPP is located 2, 3, 4, 5, 6, 7, 8, 9, 10, 11, 12, 13, 14, 15, 16, 17, 18, 19, or 20 amino acid residues distal from said selected molecule or agent.

13. A method for transporting at least one selected molecule or agent across a cellular membrane, comprising co-joining or conjugating said CPP according to claim 1 to said at least one selected molecule or agent to be transported, and contacting the complex comprising the CPP and the selected molecule or agent with the cellular membrane.

14. A therapeutic comprising at least one CPP according to claim 1 co-joined or conjugated to a selected therapeutic agent.

15. The therapeutic according to claim 14, wherein said therapeutic is selected from the group consisting of: a small molecule chemical inhibitor or activator, a protein, a supramolecular particle, a peptide, a plasmid DNA, a nucleic acid, siRNA, an antisense oligonucleotide, a chemical entity, a therapeutic drug, and an antibody.

16. A combination therapeutic comprising at least one therapeutic according to claim 14 and at least one further therapeutic agent.

17. A pharmaceutical composition comprising a therapeutic according to claim 14 and a pharmaceutically acceptable carrier.

18. A method for producing the CPP according to claim 1, the method comprising culturing a host cell transformed with a nucleic acid molecule encoding said CPP, and harvesting said CPP.

19. A pharmaceutical composition comprising a combination therapeutic according to claim 16 and a pharmaceutically acceptable carrier.

20. A cell penetrating peptide (CPP) for transporting a selected molecule or agent across a cellular membrane, wherein the CPP consists of the amino acid sequence of SEQ ID NO: 1.

* * * * *